United States Patent [19]

Lyle et al.

[11] Patent Number: 5,080,883
[45] Date of Patent: Jan. 14, 1992

[54] 99 MTCN3S-CONJUGATED ANTI-BIBRIN MONOCLONAL ANTIBODY AS AN IN VIVO DIAGNOSTIC AGENT FOR IMAGING

[75] Inventors: Leon R. Lyle, Webster Groves; Kathleen M. Miller, St. Louis, both of Mo.

[73] Assignee: Mallinckrodt, Inc., St. Louis, Mo.

[21] Appl. No.: 522,344

[22] Filed: May 11, 1990

[51] Int. Cl.$^5$ .................. A61K 49/02; A61K 39/395
[52] U.S. Cl. .................................... 424/1.1; 530/388; 530/390
[58] Field of Search .......................... 424/1.1; 534/14; 530/388, 390

[56] References Cited

U.S. PATENT DOCUMENTS 4,421,735 12/1983 Haber et al. .................... 424/1

OTHER PUBLICATIONS

Rosebrough, S.F., et al., "Aged Venous Thrombi: Radioimmunoimaging with Fibrin-specific Monoclonal Antibody", *Radiology* 1987, 162, pp. 575–577.
Wasser, M.N.J.M., et al., "An In Vitro Model for the Scintigraphic Detection of Thrombi Using a 99m Tc$^m$-Labeled Antifibrin Monoclonal Antibody", *Nuclear Medicine Communications* 1989, 10, pp. 653–659.
Koblik, P.D., et al., "Current Status of Immuno-Scintigraphy in the Detection of Thrombosis and Thromboembolism", *Seminars in Nuclear Medicine* 1989, vol. XIX, No. 3, pp. 221–237.
Knight, L. C., et al., "Evaluation of In-III Labeled Anti-Fibrin Antibody for Imaging Vascular Thrombi", *Scientific Papers* 1986, vol. 27, No. 6, p. 975.
Tymkewycz, P. M. et al., "Imaging of Human Thrombi in the Rabbit Jugular Vein: I: Comparison of Two Fibrin-Specific Monoclonal Antibodies", *Thrombosis Research* 1989, vol. 54, No. 5, pp. 411–421.
Pauwels, E. K. J., et al., "Imaging of Thrombi with Tc-99m Labeled Fibrin-Specific Monoclonal Antibody in a Rabbit Model", *Scientific Papers* 1986, vol. 27, No. 6, p. 975.

*Primary Examiner*—John S. Maples
*Attorney, Agent, or Firm*—Rita E. Downard

[57] ABSTRACT

A diagnostic composition suitable for administration to a warm-blooded animal comprising a whole, fragmented, or recombinant MH-1 monoclonal antibody labeled with a Tc-99m triamide thiolate (N$_3$S) bifunctional chelate capable of intravenous injection into an animal to produce reliable visual imaging of thrombi.

8 Claims, No Drawings

99 MTCN3S-CONJUGATED ANTI-BIBRIN MONOCLONAL ANTIBODY AS AN IN VIVO DIAGNOSTIC AGENT FOR IMAGING

FIELD OF THE INVENTION

The present invention relates generally to the preparation of a technetium-99m labeled monoclonal antibody for in vivo diagnostic use. More specifically, the invention relates to the preparation of a fibrin-specific MH-1 monoclonal antibody and then labeling the antibody with a Tc-99m triamide thiolate (N$_3$S) bifunctional chelate for intravenous injection into an animal for reliable visual imaging of thrombi. The present invention also provides a method of performing a diagnostic procedure for the in vivo administration to a warm-blooded animal and the subsequent visual imaging of thrombi.

BACKGROUND OF THE INVENTION

Monoclonal Antibodies

The first monoclonal antibody-producing hybridomas were the results of techniques devised by Kohler and Milstein (G. Kohler and C. Milstein, 1975, Nature 256: 495–497; 1976 Eur. J. Immunol. 6: 511–519). By fusing antibody forming cells with myeloma cells, Kohler and Milstein created a hybrid cell line arising from a single-fused cell hybrid which had inherited certain characteristics of both the lymphocytes and the myeloma cell lines. Like lymphocytes, the hybridomas secrete a single type of immunoglobulin specific to the antigen. Like the myeloma cells, the hybrid cells have the potential for indefinite cell division. The combination of these two features offer distinct advantages over conventional antisera. Conventional antisera derived from vaccinated animals is a heterogeneous mixture of polyclonal antibodies which cannot be reproduced identically whereas monoclonal antibodies are specific, homogeneous immunoglobulins derived from a single hybridoma cell. Any given clone produces identical antibodies. The hybridoma cell line is easily propagated in vitro or in vivo to yield monoclonal antibodies in extremely high concentrations. The hybridoma secretes an immunoglobulin specific to one and only one antigenic determinant, or epitope, on the antigen, a complex molecule having a multiplicity of antigenic determinants. For example, if an antigen is a protein, the antigenic determinant may be one of many peptide sequences, of approximately six to seven amino acids in length, within the entire protein of the molecule. Monoclonal antibodies thereby raised against a single antigen may be distinct from each other depending on the determinant that stimulated their formation.

Up until this time, several diagnostic methods have been devised to measure the in vivo concentrations of fibrin, fibrinogen and their derivatives for the diagnosis and treatment of vascular disorders, such as deep vein thrombosis and disseminated intravascular coagulation. Many of these diagnostic methods have been devised based on the production of polyclonal antisera to fibrin and fibrinogen derivatives. With the advent of hybridoma technology, monoclonal antibodies have been designed to be directed to individual antigenic sites. However, reports indicate that the problem in trying to produce an antisera remains to be a lack of specificity due to the relatively small differences between fibrinogen and fibrin and the number of neoantigenic sites, which is the inherent problem of producing antisera specific to fibrin, fibrinogen and their derivatives.

MECHANISM OF THROMBIN

The clotting process of blood may be described as the conversion of fibrinogen into fibrin by thrombin. Thrombin is a proteolytic enzyme and fibrinogen, a 340-kDal protein, is a dimer consisting of three pairs of polypeptide chains, A$\alpha$, B$\beta$, and $\gamma$, linked by disulfide bridges.

Thrombin cleaves four arginine-glycine peptide bonds in the globular portions of fibrinogen to release A and B peptides called fibrinopeptides. Fibrinogen molecules cleaved and devoid of these fibrinopeptides are called fibrin monomers which spontaneously assemble into ordered fibrous arrays called fibrin. This fibrin clot is stabilized by the formation of covalent cross-links between the side chains of the molecules in the fibrin fiber.

The formation of fibrin clots within intact blood vessels, as might be the case with thromboembolic conditions such as myocardial infarction, deep vein thrombosis, pulmonary emboli and disseminated intravascular coagulation, has been hypothesized to be caused by a hyperactive clotting mechanism wherein small changes to vessel walls trigger the coagulation cascade. The fibrin clots so formed could grow and block an entire vessel resulting in damage to other tissue.

Therefore, a need exists for a method of in vivo imaging of thrombi for life-saving diagnostic use.

SUMMARY OF THE INVENTION

Metal radionuclide-labeled fibrin-specific proteins are employed for the diagnosis of physiological conditions such as deep venous thrombosis. Fibrin-specific proteins include monoclonal antibodies or fragments thereof, plasminogen activators, and matrix or adhesion molecules such as fibronectins. The radionuclide-labeled proteins of the present invention employ a fibrin-specific monoclonal antibody, MH-1 developed by American Biogenetic Sciences, Inc., assigned U.S. patent application Ser. No. 364,053. The MH-1 monoclonal antibody was produced by fusion of splenocytes from antigen free BALB/c mice, immunized with fibrin, and NS-1 myeloma cells. The resulting MH-1 monoclonal antibody recognizes an epitope on cross-linked fibrin and binds with an affinity of approximately $6.7 \times 10^{-10}$ M. However, this monoclonal antibody does not bind to fibrinogen nor does it bind to oligopeptides in fibrin degradation products, in contrast to other reported antifibrin monoclonal antibodies. These properties make the radiolabeled whole, fragmented, or recombinant MH-1 monoclonal antibody useful as an in vivo diagnostic agent to image thrombi. The radiolabeled MH-1 monoclonal antibody specifically binds to the fibrin located at the site of a thrombus and does not bind to degradation products in the blood stream, thus leading to rapid blood clearance and improved visualization of thrombi.

The MH-1 monoclonal antibody is radiolabeled with Tc-99m using a pre-formed bifunctional chelate approach described in European Patent Application No. 88104755.9. The chelate of the present invention is a multidentate organic compound with three amide nitrogen atoms and one thiolate sulfur atom (N$_3$S chelate) bonded to the metal radionuclide, $^{99m}$Tc, which is also bonded to one oxygen atom.

DETAILED DESCRIPTION OF THE INVENTION

The monoclonal antibody employed in the present invention was the MH-1 monoclonal antibody described in U.S. patent application Ser. No. 364,053. The MH-1 monoclonal antibody was radiolabeled with a technetium-99m chelating compound of an active ester of a sulfur protected mercaptoacetyladipoylglycylglycine bifunctional chelate. In the present invention, the active ester was tetrafluorophenylester and the sulfur protecting group was ethoxyethyl.

Other common esters which find use with this labeling technique are o- and p-nitrophenyl, 2-chloro-4-nitrophenyl, cyanomethyl, 2-mercaptopyridyl, hydroxybenztriazole, N-hydroxy succinimide, trichlorophenyl, tetrafluorophenyl, thiophenyl, tetrafluorothiophenyl, o-nitro-p-sulfophenyl, N-hydroxy phthalimide and the like. For the most part, the esters will be formed from the reaction of the carboxylate with an activated phenol, particularly nitro-activated phenols, or a cyclic compound based on hydroxylamine. The advantages of using sulfur protecting groups include the fact that a separate step for removal of the sulfur-protective groups is not necessary. The protecting groups are displaced from the compound during the radiolabeling in what is believed to be metal-assisted acid cleavage: i.e., the protective groups are displaced in the presence of the metal radioisotope at an acidic pH and the radioisotope is bound by the chelating compound. The radiolabeling procedure thus is simplified, which is especially advantageous when the chelating compounds are to be radiolabeled in a hospital laboratory shortly before use. In addition, the basic pH conditions and harsh conditions associated with certain known radiolabeling procedures or procedures for removal of other sulfur protective groups are avoided. Thus, base-sensitive groups on the chelating compound survive the radiolabeling step intact. Suitable sulfur protecting groups, when taken together with the sulfur atom to be protected, include hemithioacetal groups such as ethoxyethyl, tetrahydrofuranyl, methoxymethyl, and tetrahydropyranyl. Other suitable sulfur protecting groups are acyl groups, preferably alkanoyl or benzoyl. Other possible formulas for the metal chelating compounds are described in the European Patent Application assigned publication number 0 284 071.

Synthesis of the Tc-99m bifunctional chelate and subsequent conjugation to a monoclonal antibody can be performed as described in the European Patent Application assigned publication number 0 284 071.

The purified technetium-99m labeled MH-1 monoclonal antibody was injected into the femoral vein of rabbits with experimentally induced thrombi in the jugular vein. The TC-99m MH-1 monoclonal antibody reliably visualized thrombi within two and one half (2.5) hours post-injection. This result indicates that the MH-1 monoclonal antibody, when radiolabeled with a Tc-99m triamide thiolate bifunctional chelate, is efficacious as an in vivo diagnostic agent for the imaging of thrombi.

EXAMPLE I

Preparation of Tc-99m N$_3$S-MH-1 Monoclonal Antibody

The Tc-99 bifunctional chelate complex of the tetrafluorophenyl ester of S-ethoxyethyl mercaptoadipoylglycylglycine (N$_3$S-adipyl-TFP-ester) was prepared by reduction of Tc-99m pertechnetate with 120 mg stannous chloride dihydrate in the presence of 5 mg sodium gluconate and 100 mg of the N$_3$S-adipyl-TFP-ester at pH 3. The solution was heated for 15 minutes in a 75° C. water bath, then placed into ice for five minutes. This reaction gave 86% of $^{99m}$TcN$_3$S-TFP-ester complex as determined by HPLC (Alltech Adsorbosphere C$_{18}$, 25 cm × 4.6 mm, 5 micron; 24% acetonitrile: 76% Dulbecco's modified phosphate buffered saline; 1 ml/min; retention times 8.2 minutes and 14.5 minutes).

A C$_{18}$ Sep-Pak ® (Waters) was rinsed once with 3 ml of ethanol and then twice with 3 ml of water. The $^{99m}$TcN$_3$S solution was diluted to 10 ml with PBS and then loaded onto the Sep-Pak ®. The Sep-Pak ® was rinsed in succession with 3 ml of 2.5% ethanol/97.5% PBS, 0.5 ml methanol, and 1.5 ml methanol. The 1.5 ml methanol fraction was then evaporated to dryness. For conjugation of the complex active ester to the antibody, 0.4 ml of 1.48 mg MH-1/1.0 ml 0.1M phosphate, pH 10 was added to the evaporated vial containing the $^{99m}$TcN$_3$S adipyl-TFP-ester complex. The solution was incubated at 37° for 15 minutes.

A PD-10 gel filtration column (Pharmacia LKB) was equilibrated with PBS. The $^{99m}$TcN$_3$S-MH-1 preparation was loaded onto the column and the column was eluted with PBS and 0.5-1.0 ml fractions collected. The fractions were analyzed to determine the percentage of $^{99m}$Tc bound to the protein using ITLC with 12.5% trichloroacetic acid as the developing solvent ($^{99m}$Tc-labeled protein remains at the origin) and fractions with >90% radio-activity on the protein according to ITLC were combined. The combined fractions were further characterized with HPLC (Zorbax ® gel filtration column (DuPont), 0.1M phosphate, 0.1% SDS; 1 ml/min; $^{99m}$Tc-protein retention time 7.6 minutes). The purity of $^{99m}$TcN$_3$S-adipyl-MH-1 was 99%.

EXAMPLE II

Utilization of Tc-99m N$_3$S-MH-1 Monoclonal Antibody

The technetium-99m labeled MH-1 monoclonal antibody (120 microcurie/microgram) was injected into rabbits (200 to 400 mCi/kg) with experimentally induced thrombi. Serial scintigrams and arterial blood samples were acquired for six (6) hours; tissues and thrombi were assayed for technetium-99m concentration. Clot-to-blood ratios were determined as were half-lives of tracer elimination from the blood. These results were then compared to those for a technetium-99m labeled antibody not reactive for fibrin, technetium-99m NR-Lu-10. Technetium-99m NR-Lu-10 is a monoclonal antibody that is specific for an antigen found on several carcinomas. The technetium-99m MH-1 monoclonal antibody reliably visualized thrombi within two and one half (2.5) hours post-injection; the technetium-99m NR-Lu-10 did not image thrombi at any time. Analysis of the technetium-99m concentrations produced these results:

| n | TC-99m MH-1 4 | Tc-99m NR-Lu-10 2 |
|---|---|---|
| clot-to-blood ratio | 16.3 (range: 8.7–28.3) | 0.19 (range: 0.18–0.21) |
| t ½ (hours) | 3.7 (range: 3.1–4.0) | 11.3 (range: 9.6–13.5) |

The clot-to blood ratios for technetium-99m MH-1 at six (6) hours post-injection are comparable to or higher than values obtained after much longer periods (18–48 hours) for other currently available radiolabeled antifibrin monoclonal antibodies. The clot-to-blood ratios of the fibrin specific Tc-99m MH-1 monoclonal antibody exceeds that of the non-specific Tc-99m NR-Lu-10 antibody on average, by a factor of 85. The $t_{\frac{1}{2}}$ for technetium-99m MH-1 is considerably shorter than is normally found for whole monoclonal antibodies and might relate to the acidic isoelectric point (pI=5.8) of the MH-1 monoclonal antibody or be due to extraction from the blood by the liver. These results illustrate the outstanding properties of the present invention being that technetium-99m MH-1 monoclonal antibody is efficacious as an in vivo diagnostic agent for the imaging of thrombi.

In order to image thrombi, a preparation of the present invention using either whole, fragmented, or recombinant MH-1 monoclonal antibodies is administered to the patient, for example, in the form of an injectable liquid. By means of suitable detectors, e.g. a gamma camera, images can be obtained by recording the emitted radiation of the organ or the pathological process in which the radioactive material has been incorporated, which in the present case is thrombi.

The $^{99m}$TcN$_3$S-adipyl MH-1 monoclonal antibody of the present invention or a fragment or recombinant thereof prepared as described above provides a means of in vivo diagnostic imaging of thrombi which provides many advantages over prior known procedures which could only be used to calculate the in vivo concentrations of blood proteins.

After the MH-1 monoclonal antibody is prepared and labeled according to the procedure described, the composition is used with a pharmaceutically acceptable carrier in a method of performing a diagnostic imaging procedure using a gamma camera or like device which involves injecting or administering to a warm-blooded animal an effective amount of the present invention and then exposing the warm-blooded animal to an imaging procedure as described above, thereby imaging at least a portion of the body of the warm-blooded animal.

Pharmaceutically acceptable carriers include those that are suitable for injection such as aqueous buffer solutions, e.g. tris(hydroxymethyl)aminomethane (and its salts), phosphate, citrate, bicarbonate, etc., sterile water for injection, physiological saline, and balanced ionic solutions containing chloride and/or bicarbonate salts of normal blood plasma cations such as $Ca^{2+}$, $Na^+$, $K^+$ and $Mg^{2+}$. Other buffer solutions are described in *Remington's Practice of Pharmacy*, Eleventh Edition, for example on page 170. The carriers may contain a chelating agent, e.g. a small amount of ethylenediaminetetraacetic acid, calcium disodium salt, or other pharmaceutically acceptable chelating agents.

The concentration of the labeled monoclonal antibodies in the pharmaceutically acceptable carrier, for example an aqueous medium, varies with the particular field of use. A sufficient amount is present in the pharmaceutically acceptable carrier in this particular case when satisfactory visualization of the thrombi is achievable.

The composition is administered to the warm-blooded animal so that the composition remains in the living animal body for about 6 to 7 hours, although shorter and longer residence periods are normally acceptable.

The technetium-99m MH-1 monoclonal antibodies may be used in the usual way in imaging procedures. For example, with the present invention when imaging thrombi, a sufficient amount of the radiolabeled MH-1 antibody must be intraveneously administered to the warm-blooded animal to provide adequate visualization; the animal or a portion thereof is then scanned with a suitable imaging machine such as a gamma camera.

After consideration of the above specification, it will be appreciated that many improvements and modifications in the details may be made without departing from the spirit and scope of the invention. It is to be understood, therefore, that the invention is in no way limited, except as defined by the appended claims.

We claim:

1. A diagnostic composition suitable for administration to a warm-blooded animal comprising a whole, fragmented, or recombinant MH-1 monoclonal antibody labeled with a Tc-99m triamide thiolate (N$_3$S) bifunctional chelate for intravenous injection into an animal to produce reliable visual imaging of thrombi.

2. The diagnostic composition of claim 1 wherein said Tc-99m triamine thiolate (N$_3$S) bifunctional chelate is a tetrafluorophenyl ester of S-ethoxyethylmercaptoacetylaminoadipolyglycylglycine.

3. A method of performing a diagnostic procedure, which comprises administering to a warm-blooded animal an imaging-effective amount of a whole, fragmented or recombinant MH-1 monoclonal antibody labeled with a Tc-99m triamide thiolate (N$_3$S) bifunctional chelate to allow for visual imaging of thrombi.

4. The method of performing the diagnostic procedure of claim 3 wherein said Tc-99m triamide thiolate (N$_3$S) bifunctional chelate is a tetrafluorophenyl ester of S-ethoxyethylmercaptoacetylaminoadipolyglycylglycine.

5. A whole, fragmented, or recombinant MH-1 monoclonal antibody labeled with a Tc-99m triamide thiolate (N$_3$S) bifunctional chelate for intravenous injection into a warm-blooded animal to produce reliable visual imaging of thrombi.

6. The whole, fragmented or recombinant MH-1 monoclonal antibody of claim 5 wherein said Tc-99m triamide thiolate (N$_3$S) bifunctional chelate is a tetrafluorophenyl ester of S-ethoxyethylmercaptoacetylaminoadipolyglycylglycine.

7. The whole, fragmented, or recombinant MH-1 monoclonal antibody of claims 1, 3, or 5 wherein said MH-1 monoclonal antibody labeled with a Tc-99m triamide thiolate (N$_3$S) bifunctional chelate is for injection into a warm-blooded animal to produce reliable visual imaging of thrombi within two and one half hours post-injection.

8. The whole, fragmented or recombinant MH-1 monoclonal antibody of claim 7 wherein said Tc-99m triamide thiolate (N$_3$S) bifunctional chelate is a tetrafluorophenyl ester of S-ethoxyethylmercaptoacetylaminoadipolyglycyglycine.

* * * * *

UNITED STATES PATENT AND TRADEMARK OFFICE
CERTIFICATE OF CORRECTION

PATENT NO. : 5,080,883

DATED : Jan. 14, 1992

INVENTOR(S) : Leon R. Lyle, Kathleen M. Miller

It is certified that error appears in the above-identified patent and that said Letters Patent is hereby corrected as shown below:

On title page, item [54] and col. 1, line 2, in the title,
"99MTCN3S-" should be --$^{99m}TcN_3S$- --

Column 1, line 1
"Anti-Bibrin" should be --Anti-Fibrin--

Column 1, line 9
"in vivo" should be --$\underline{in\ vivo}$--

Column 1, line 16
"in vivo" should be --$\underline{in\ vivo}$--

Column 1, line 43
"in vitro or in vivo" should be --$\underline{in\ vitro}$ or $\underline{in\ vivo}$--

Column 1, line 56
"in vivo" should be --$\underline{in\ vivo}$--

Column 2, line 30
"in vivo" should be --$\underline{in\ vivo}$--

Column 2, lines 54, 55
"in vivo" should be --$\underline{in\ vivo}$--

Column 3, line 14
"o- and p-" should be --$\underline{o}$- and $\underline{p}$- --

Column 3, line 18
"o-" should be --$\underline{o}$- --

Column 3, line 60
"in vivo" should be --$\underline{in\ vivo}$--

UNITED STATES PATENT AND TRADEMARK OFFICE
CERTIFICATE OF CORRECTION

PATENT NO. : 5,080,883
DATED : January 14, 1992
INVENTOR(S) : Leon R. Lyle, Kathleen M. Miller It is certified that error appears in the above-identified patent and that said Letters Patent is hereby corrected as shown below:

Column 5, line 14
 "in vivo" should be --*in vivo*--

Column 5, line 28
 "in vivo" should be --*in vivo*--

Column 5, line 30
 "in vivo" should be --*in vivo*--

Signed and Sealed this

Eighth Day of February, 1994

Attest:

BRUCE LEHMAN

*Attesting Officer*          *Commissioner of Patents and Trademarks*